United States Patent
Guedeney et al.

(10) Patent No.: US 6,181,972 B1
(45) Date of Patent: Jan. 30, 2001

(54) HIGH IMPEDANCE LEAD FOR IMPLANTABLE MEDICAL DEVICES

(76) Inventors: Dominique Guedeney, 5 pente d'Etaux, 78470 Saint Remy de Chevreuse (FR); Alain Bailly, 69 avenue du General Leclerc, 75014 Paris (FR)

( * ) Notice: Under 35 U.S.C. 154(b), the term of this patent shall be extended for 0 days.

(21) Appl. No.: 09/291,139

(22) Filed: Apr. 12, 1999

(30) Foreign Application Priority Data

Apr. 15, 1998 (FR) .................................................. 98 04677

(51) Int. Cl.[7] .................................................. A61N 1/05
(52) U.S. Cl. .................................................. 607/121
(58) Field of Search .................. 607/121–128; 600/373–375, 381

(56) References Cited

U.S. PATENT DOCUMENTS

| | | | |
|---|---|---|---|
| 4,784,161 | 11/1988 | Skalsky et al. | 128/785 |
| 4,917,106 | 4/1990 | Olivier | 128/785 |
| 5,259,394 | 11/1993 | Bens | 607/127 |
| 5,300,107 | 4/1994 | Stokes et al. | 607/126 |
| 5,443,492 | 8/1995 | Stokes et al. | 607/131 |
| 5,466,255 | 11/1995 | Franchi | 607/128 |
| 5,609,623 * | 3/1997 | Lindegren | 607/128 |
| 5,645,580 * | 7/1997 | Moaddeb et al. | 607/122 |
| 5,800,499 | 9/1998 | Ollivier | 607/126 |
| 5,814,005 | 9/1998 | Barra et al. | 604/8 |

FOREIGN PATENT DOCUMENTS

| | | | |
|---|---|---|---|
| 0622090 | 11/1994 | (EP) | A61N/1/05 |
| 0791372 | 8/1997 | (EP) | A61N/1/05 |
| 2607013 | 5/1988 | (FR) | A61N/1/05 |
| 2096001 | 10/1982 | (GB) | A61N/1/04 |

OTHER PUBLICATIONS

J.C. Daubert, et al.; "Quel avenir pour la stimulation comme traitement primaire de l'insuffisance cardiaque?", *Stimuvoeur*, 1997, vol. 25, issue 3, pp. 170–176.

* cited by examiner

*Primary Examiner*—Jeffrey R. Jastrzab

(57) ABSTRACT

A lead with an increased impedance for an active implantable medical device, in particular for a pacemaker. The lead comprises a cylindrical body (14) presenting at its distal end a contact surface (30) for making contact with the endocardium, which is electrically insulated, and a stimulation electrode (16), which is electrically conducting and which is connected to a conductor of the lead. The electrode (16) has at least one active element (22), for example, a plurality of protuberances (22), each one presenting at least an exposed extremity tip (26) having a hemispherical area, making a ledge compared to the contact surface (i.e., protruding) therefrom. The active element presents on at least a part of its exposed extremity to be placed in contact with the endocardium a radius of curvature less than 0.5 mm, more preferably less than or equal to 0.3 mm. With a microporous vitreous carbon as the material of the protuberances, one can at least increase the contact impedance of the lead at the heart/electrode interface to 800 Ohm, preferably up to approximately 1000 Ohm. An annular flat form or disc-shaped active element also can be used as an alternative to the protuberance(s).

34 Claims, 2 Drawing Sheets

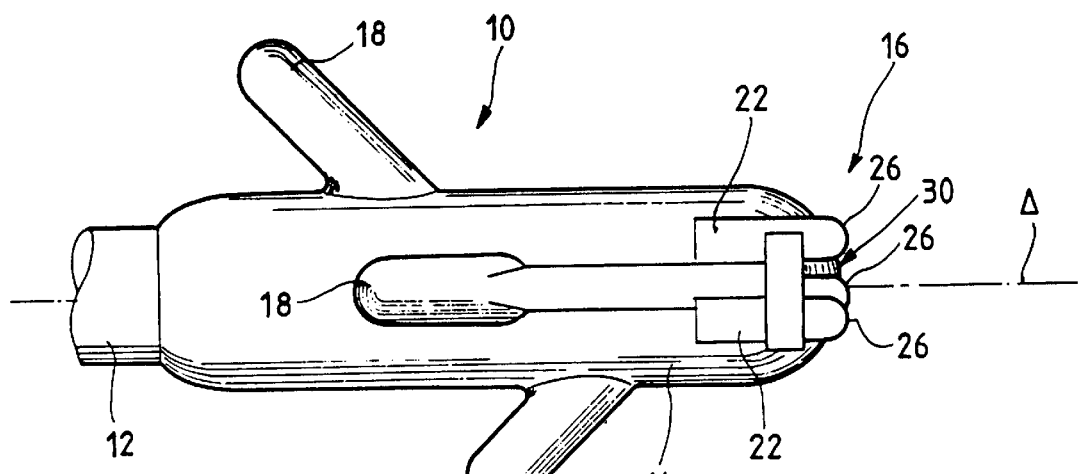
FIG_1
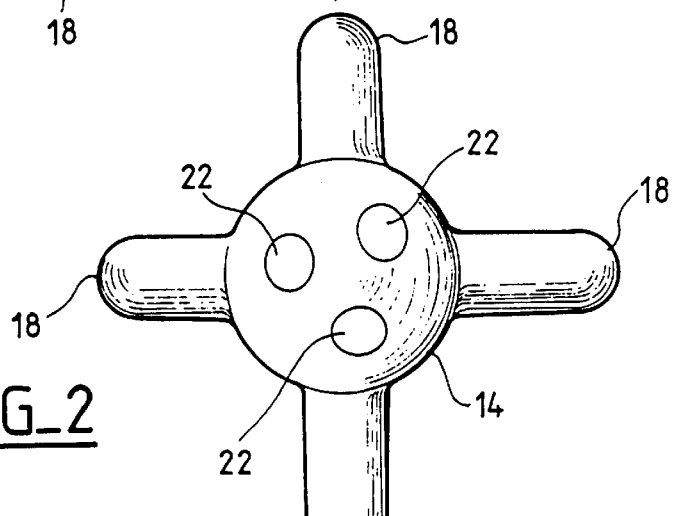
FIG_2
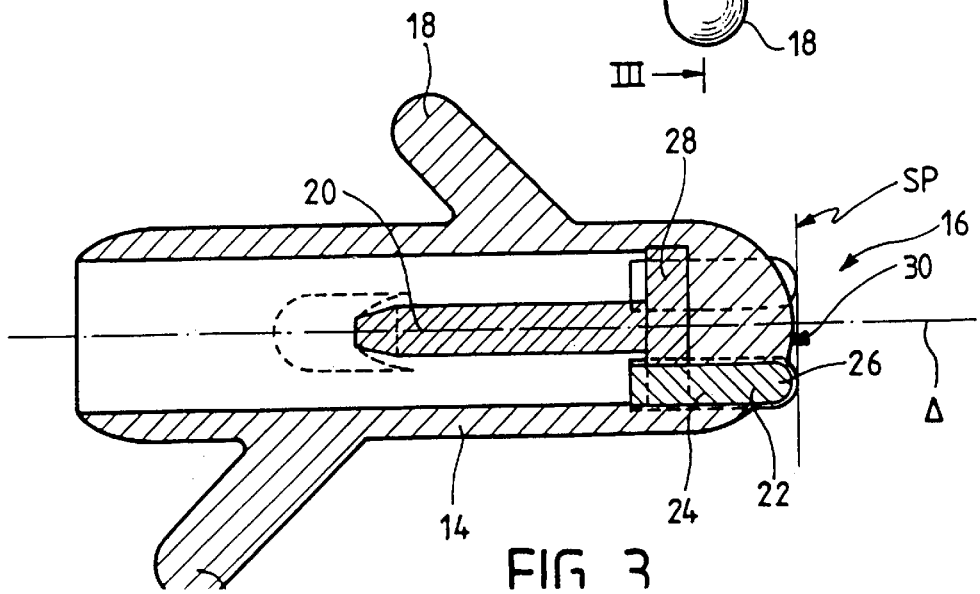
FIG_3

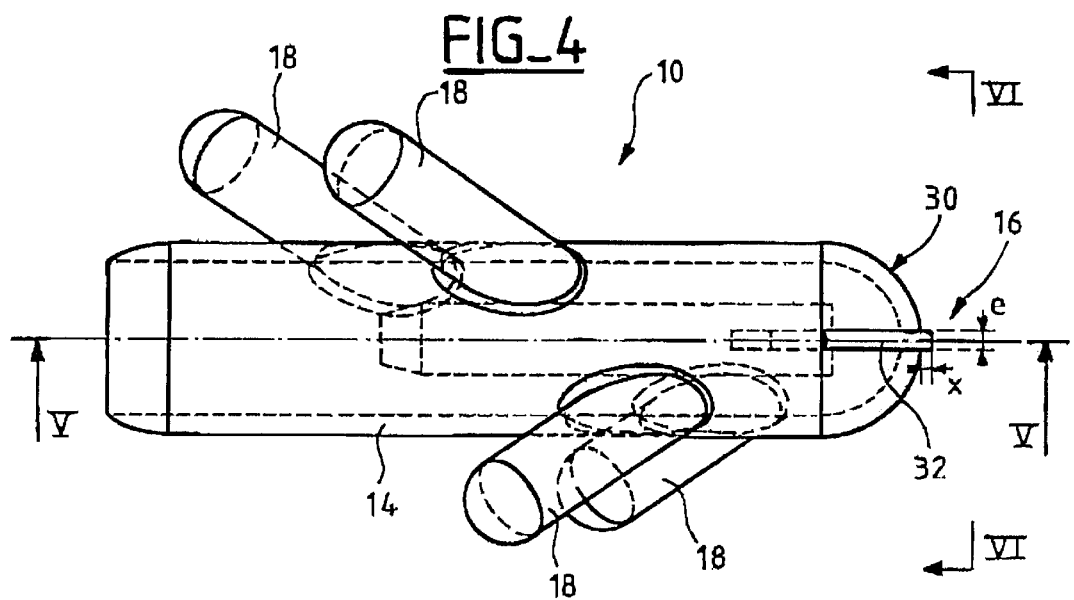
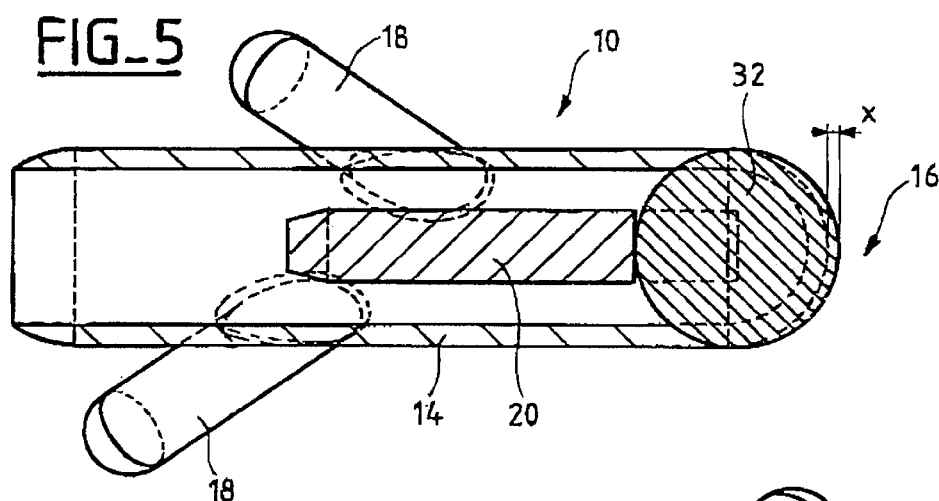
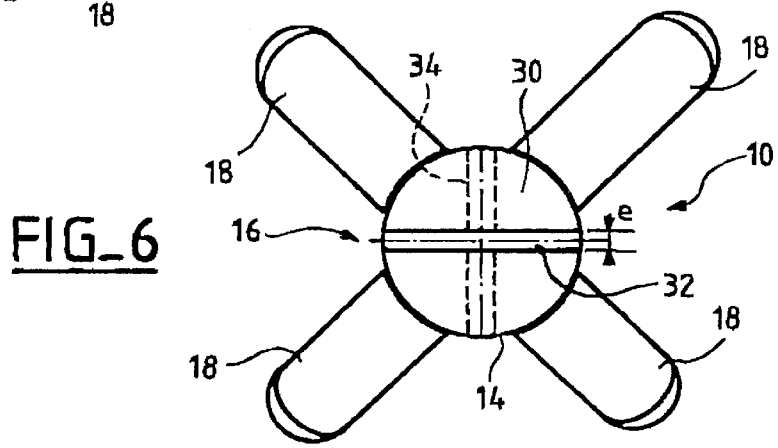

HIGH IMPEDANCE LEAD FOR IMPLANTABLE MEDICAL DEVICES

FIELD OF THE INVENTION

The present invention relates to leads for implantable medical devices, more particularly, cardiac stimulation leads.

BACKGROUND OF THE INVENTION

Typically, cardiac stimulation leads comprise a hollow insulating sleeve in a flexible material with an internal electric conductor (two conductors in the case of a bipolar lead), finished at its distal extremity by a bearing surface which is intended to come in contact with the endocardium. The bearing surface is equipped with an electrode (the so-called "distal" electrode in the case of a bipolar lead), making it possible to carry out the stimulation of the myocardium. The distal stimulation electrode generally presents a flattened frontal extremity, constituting an active surface, in touching contact with the wall of the myocardium. The design of such an extremity of the lead must satisfy various requirements, which, until now, have been contradictory.

The first requirement, which is essential, is to provide a high impedance at the heart/electrode interface, in order to decrease the current necessary for the stimulation and, consequently, to increase the lifespan of the pulse generator. To increase the interface impedance, it is desirable to reduce the dimensions of the active surface of the stimulation electrode (see, in particular, Clémenty et al. *Économies d'énergie: le rôle de la sonde* [*Energy Saving: The Role of the Lead*], Stimucoeur 1998, 26 no. 4, pp. 184–187).

However, a reduction in the dimensions of the lead extremity involves an increase in the pressure at the heart/electrode interface leading to increases in the stimulation threshold, and potentially to perforations of the myocardium.

In one particular known geometry, the stimulation electrode is a ring which has a flattened annular surface a flattened frontal (distal) end, whose central area is insulated. One can thus have a current conducting surface without reducing the total surface area (conducting and non-conducting) bearing against the endocardium. This structure reflects a first compromise solution as between the aforementioned constraints.

In addition, the choice of a material for the electrode, such as a microporous vitreous carbon in the place of a metal, e.g., platinum, makes it possible to combine an excellent biocompatibility with satisfactory electric performance (in particular, low energy losses by polarization). However, even in this case, the contact impedance remains relatively low, about 500 Ohm.

Further, the annular shape of the electrode leads to losses of current directly in blood, through the part of the ring which is not in contact with the myocardium. This constitutes an additional factor, prejudicial to the lifespan of the pulse generator, from the reduction in the impedance of contact.

OBJECTS AND SUMMARY OF THE INVENTION

It is, therefore, an object of the present invention to propose a lead structure which makes it possible to alleviate the aforementioned disadvantages, having a high contact impedance, preferably easily being able to reach 1000 Ohm, while maintaining an optimal surface contact between the electrode and the endocardium. Thus, it also will be seen that a preferred structure of the present invention makes it possible to take advantage of a particular phenomena likely to improve still further the effectiveness of a stimulation, in particular, the application of "point effects" and the presence of high potential gradients. These advantages, as they will become apparent, are obtained with a structure which advantageously provides very little trauma for the patient, thus minimizing any risk of perforation of the myocardium.

To this end, the lead of the present invention broadly concerns a cylindrical body presenting a distal end and a contact surface for making contact with the endocardium, which contact surface is electrically insulated, and a stimulation electrode, which is electrically conducting, and connected to a conductor of the lead. The stimulation electrode is characterized in that it comprises at least one active element presenting at its exposed (distal) extremity a protrusion relative to the body contact surface, wherein the active element presents, on at least a part of its protruding surface to be maintained in contact with the endocardium, a radius of curvature less than 0.5 mm, preferably less than or equal to 0.3 mm. It should be understood that the protrusion is a projecting body, namely one that provides a step or surface discontinuity as between the active element and the contact surface.

Very advantageously, the contact impedance of the lead at the heart/electrode interface, when the lead is conventionally installed in a patient's heart, is at least 800 Ohm, more preferably approximately 1000 Ohm.

The material of the active element is preferably a microporous vitreous carbon.

In a first embodiment, the lead of the present invention includes an active element which is a plurality of active elements each having a distinct shape, also called a "protuberance", which includes an exposed distal extremity tip. The exposed extremity tip projects outwardly from the contact surface. The plurality of protuberances are mechanically interconnected and the distal extremity tips of two adjacent protuberances are separated by an interval defined by a part of the contact surface, and thus the endocardium when the lead is fixed in position against the endocardium.

According to various alternative implementations, this first embodiment may include one or more of the following features: the extremity area each of active element protuberance is hemispherical. The contact surface of the lead to be placed in contact with the endocardium is hemispherical. Each of the active element protuberances is located at a distance from an axis of the lead and regularly distributed around this axis; preferably there are three protuberances equiangularly distributed at 120° around an axis of the lead. Each protuberance preferably comprises a cylindrical stem whose diameter lies between 15% and 30% of the diameter of the contact surface. The exposed distal extremity of the protuberances are approximately coplanar, the distal extremity of the contact surface is preferably approximately located in the plane of the exposed extremities of the protuberances.

In accordance with a second embodiment of the invention, the active element of the lead of the present invention is an element having a flat form preferably extending in a radial plane, from the lead extremity lead, while protruding from the contract surface along a meridian thereof. When the surface contact is hemispherical, the active element can be in the shape of a flat disc.

One also can envisage two active elements of a flat form, preferably extending in two orthogonal radial planes from the lead extremity. Other configurations and structures are possible as will be understood by a person of ordinary skill in the art in view of the discussion which follows.

BRIEF DESCRIPTION OF THE DRAWINGS

Other features, characteristics and advantages of the present invention will appear to the person of ordinary skill in the art in view of the detailed description below, made with reference to the annexed drawings, in which like reference numerals refer to like elements, and in which:

FIG. 1 is a side view of an extremity of a lead according to a first embodiment of the invention;

FIG. 2 is an end view of the lead of FIG. 1;

FIG. 3 is a longitudinal sectional view, taken along line III—III of FIG. 2;

FIG. 4 is a side view of an extremity of a lead according to a second embodiment of the present invention;

FIG. 5 is a longitudinal sectional view, taken along line V—V of FIG. 4; and

FIG. 6 is an end view of the lead of FIG. 4.

DETAILED DESCRIPTION OF THE DRAWINGS

With reference to the figures, reference 10 indicates in a general way the distal extremity of a pacemaker lead, which comprises, at the extremity of a flexible insulating sleeve 12 encapsulating a metal conductor (two conductors in the case of a bipolar lead), an isolating body 14 of a generally cylindrical form terminating at a surface intended to come in contact with the internal wall of the myocardium and carrying a conducting electrode for stimulation (and, possibly, detection). The cylindrical body 14 and the insulating sleeve 12 are made of an electrically insulating and, in addition, biocompatible material, generally a polyurethane or silicone elastomer. Part of the body 14 can, in addition, contain a charge of an active material such as a steroid or other drug intended to be diffused in the area of the myocardium in the vicinity of the electrode in order to improve (or to delay any degradation of) the performance of the lead after implantation. Such charges of active material are known in the art.

The body 14 is also generally equipped with anchoring barbs 18 intended to imbricate themselves in the cardiac trabecular to maintain the extremity of the lead in position after its implantation.

In other embodiments, not shown, one can envisage a system of anchoring with the lead a screw, such as are known in the art, for example, that of the lead model US46 available from ELA Médical S. A., the assignee of the present invention.

The body 14 also carries the stimulation electrode 16. Typically made of a microporous vitreous carbon, connected at is proximal side to an internal metal conductor (not illustrated) by an axial stem 20.

Referring to FIGS. 1–3, a first embodiment is illustrated. In this embodiment, at the distal end, the stimulation electrode is made of a plurality of distinct protuberances 22, for example, three as illustrated (this number, of course, not being restrictive as more or less protuberances could be employed). Each of these protuberances comprises a cylindrical stem 24, embedded in or surrounded by the material of the body 14, and having an emergent exposed tip 26 at its distal extremity. Advantageously, the exposed tip is provided with a hemispherical form. The hemispherical form ensures a good application of the protuberances 22 against the endocardiun and, in addition, avoids their penetration into the muscle because of the relatively large total surface in contact with the myocardium.

These protuberances 22 are preferably regularly or equi-angularly distributed around the axis Δ of the lead (e.g., distributed at 120° intervals in the illustrated example). Further, the distal extremities 26 of the protuberances 22 are located in a plane P (FIG. 3) oriented perpendicular to axis Δ, and passing roughly at or near the top of hemispherical contact surface 30 of the body 14. Each protuberance 22 is made out of a conducting material, typically a microporous vitreous carbon. More preferably, the protuberances 22 are mechanically joined together inside the body 14 by the intermediary of a common support part 28 interdependent of the axial stem 20. In this example, elements 22 are not only mechanically, but also electrically, united.

In one alternative variation, in a multipolar or bipolar configuration, each protrusion 22 need not be electrically connected to the same conductor, and thus can be respectively connected to distinct conductors of the lead.

Preferably, the extremity of the body 14 forming a contact surface 30 with the endocardium is provided a hemispheric form. In one particular implementation of this first embodiment, the diameter of the contact surface 30 is 2.5 mm, and the diameter of each extremity tip 26 of the three protrusions 22 has a diameter of about 0.6 mm. This results in an active surface (the surface of the electrode protruding from the body 14 and thus likely to come in contact with the myocardium) for each protuberance 22 of 0.565 $mm^2$, corresponding to a total active electrode surface of 1.695 $mm^2$.

This electrode surface areas is low as compared typically with a minimal value of 2 $mm^2$, for the known prior art leads, and yields a relatively high impedance, typically about 1000 Ohm. For the conditions of measurement of such an impedance at the heart/electrode interface, reference is made to the draft standard PR/EN 45502 "Active Implantable Medical Devices", CENELEC, Sep. 1996.

Importantly, this reduction in the active surface is obtained by preserving an excellent possibility of contact of the conducting zones with the endocardium, and is believed to be due to (i) the division of the active electrode contact surface over a plurality of individual elements regularly distributed, (ii) the hemispherical form, (iii) the optimal positioning compared to the hemispherical contact surface 30 of body 14, and (iv) the light penetration in the cardiac muscle, which contributes to a better stimulation by a more intimate contact with the active part of the electrode.

One will note several additional advantages obtained by the particular structure just described: A low radius of curvature of the protrusions, allowing one to obtain a less traumatizing lead extremity; an alternation of conducting and insulating surfaces, leading to important potential gradients, therefore a rupture of the field lines contributing (in a way in itself known) to an improvement of the stimulation phenomenon; a point effect at each of the protuberance conducting elements, this phenomenon being favorable to stimulation, given that the myocardium cells to be excited are sensitive to a difference of potential in the longitudinal direction (a phenomenon in itself known, but until now not easily implemented because of the risks of perforation of the myocardium).

It will also be noted that this first embodiment is particularly appropriate when one wishes to envisage the use of an anchoring screw to complement or in the alternative to the barbs 18. Because the area at the top of hemispherical contact surface 30 is void of protuberances 22, one can implement within it an anchoring screw without difficulty.

Referring to FIGS. 4 to 6, a second embodiment of the invention is illustrated. On the distal side, in this embodiment, the stimulation electrode 16 is made of a disc 32 of small thickness, extending in a radial plane approximately according to a semi-circumference of the hemispherical contact surface 30. In this embodiment also, disc 32 projects from contact surface 30. Disc 32 is made of a conducting material, preferably made of microporous vitreous carbon, which is connected electrically and mechanically to the axial stem 20, for example by welding.

Preferably, and in a manner which respects the dimensional tolerances indicated below, disc 32 is inserted in the distal hemispherical extremity of the lead after molding of the silicone material of body 16. In one particular embodiment, the diameter of the contact surface 30 is 2 mm, and the disc 32 is provided with a diameter of 2 mm, and a thickness e of 0.2 mm. The disc 32 is then set in the body 16 to have a projection x of 0.1 mm.

This geometry provides, as with the geometry of preceding embodiment, the following advantages. A tip extremity which is less traumatizing for the cardiac muscle. A maximum intimate contact with the surface of the endocardium, contributing to a better circulation. A low radius of curvature of the projecting members, allowing to obtain a less traumatizing lead extremity, a large potential gradient and a point effect contributing to an improvement of the stimulation phenomenon. In this respect, in this second embodiment, the point effect is located mainly on the exposed semicircular edges of disc 32.

In one implementation of this second embodiment, the carbon disc can be machined to provide without difficulty the disc edges with a radius of curvature (considered in a plane perpendicular to the disc plane) about 0.01 mm, making it possible to produce a large point effect and this on all the apparent semicircumference of the disc.

In an alternative implementation of this second embodiment, instead of a single disc 32 extending in a radial plane from the lead, one can envisage two discs laid out in a cross 32, 34 (FIG. 6), preferably extending in two orthogonal planes from the lead.

The disc or discs 32 used preferably have a flat form which may be solid (i.e., a section of a solid cylinder or sphere) or annular, and may be complete (e.g., circular) or incomplete (e.g., a half moon or crescent shape) as a matter of design choice. Further, where two or more discs are used, they may be formed from separate pieces of conducting material joined together, e.g., by welding, or cast as or machined from a unitary block of material.

One skilled in the art will appreciate that the present invention can be practiced by embodiments other than those disclosed herein, which embodiments are presented for purposes of illustration and not of limitation.

We claim:

1. A lead for an active implantable medical device having an electrical conductor, comprising:
    a cylindrical body having a distal end, an extremity, and a contact surface on said extremity, the body being made of an electrically insulated material, and
    a stimulation electrode, connected to said lead conductor, wherein the stimulation electrode comprises at least one active element having an exposed extremity tip, said exposed extremity tip protruding from said body contact surface, said active element presenting on at least a part of its exposed extremity tip a radius of curvature less than 0.5 mm;
    wherein the active element further comprises a plurality of distinct protuberances mechanically interconnected, each protuberance having an exposed extremity tip protruding from the body, the exposed extremity tips of any two adjacent protuberances being separated by an interval defined by a part of the bode contact surface, and
    wherein the exposed extremity tips of the protuberances further comprises a hemispherical surface.

2. The lead of claim 1 wherein the active element radius of curvature is not greater than 0.3 mm.

3. The lead of claim 1, wherein the lead further comprises a heart/electrode interface contact impedance of at least 800 Ohm.

4. The lead of claim 3 wherein the heart/electrode interface contact impedance comprises approximately 1000 Ohm.

5. The lead of claim 1, wherein the active element comprises a microporous vitreous carbon material.

6. The lead of claim 1, wherein the body further comprises an axis and the plurality of protuberances are respectively positioned in said body at a distance from the axis and regularly distributed around said axis.

7. The lead of claim 6, wherein the plurality of protuberances further comprise three protuberances regularly distributed at 120° intervals around the axis.

8. The lead of claim 1, in which the exposed extremity tips of the protuberances are approximately coplanar.

9. The lead of claim 1, wherein the body contact surface has a diameter and each active element protuberance further comprises a cylindrical stem having a diameter between 15% and 30% of the diameter of the contact surface.

10. A lead for an active implantable medical device having an electrical conductor, comprising:
    a cylindrical body having a distal end, an extremity, and a contact surface on said extremity, the body being made of an electrically insulated material, and
    a stimulation electrode, connected to said lead conductor, wherein the stimulation electrode comprises at least one active element having an exposed extremity tip, said exposed extremity tip protruding from said body contact surface, said active element presenting on at least a part of its exposed extremity tip a radius of curvature less than 0.5 mm,
    wherein the active element further comprises a plurality of distinct protuberances mechanically interconnected, each protuberance having an exposed extremity tip protruding from the body, the exposed extremity tips of any two adjacent protuberances being separated by an interval defined by a part of the body contact surface;
    wherein the body contact surface further comprises a hemispherical surface.

11. The lead of claim 10, wherein the body contact surface has a diameter and each active element protuberance further comprises a cylindrical stem having a diameter between 15% and 30% of the diameter of the contact surface.

12. The lead of claim 10, wherein the active element radius of curvature is not greater than 0.3 mm.

13. The lead of claim 10, wherein the lead further comprises a heart/electrode interface contact impedance of at least 800 Ohm.

14. The lead of claim 13, wherein the heart/electrode interface contact impedance comprises approximately 1000 Ohm.

15. The lead of claim 10, wherein the active element comprises a microporous vitreous carbon material.

16. The lead of claim 10, wherein the body further comprises an axis and the plurality of protuberances are respectively positioned in said body at a distance from the axis and regularly distributed around said axis.

17. The lead of claim 16, wherein the plurality of protuberances further comprise three protuberances regularly distributed at 120° intervals around the axis.

18. The lead of claim 10, in which the exposed extremity tips of the protuberances are approximately coplanar.

19. A lead for an active implantable medical device having an electrical conductor, comprising:

a cylindrical body having a distal end, an extremity, and a contact surface on said extremity, the body being made of an electrically insulated material, and a stimulation electrode, connected to said lead conductor, wherein the stimulation electrode comprises at least one active element having an exposed extremity tip, said exposed extremity tip protruding from said body contact surface, said active element presenting on at least a part of its exposed extremity tip a radius of curvature less than 0.5 mm:

wherein the active element further comprises a plurality of distinct protuberances mechanically interconnected, each protuberance having an exposed extremity tip protruding from the body, the exposed extremity tips of any two adjacent protuberances being separated by an interval defined by a part of the body contact surface and wherein the body contact surface has an extremity which is approximately coplanar with the extremity tips of the active element protuberances and in which the exposed extremity tips of the protuberances are approximately coplanar.

20. The lead of claim 19, wherein the active element radius of curvature is not greater than 0.3 mm.

21. The lead of claim 19, wherein the lead further comprises a heart/electrode interface contact impedance of at least 800 Ohm.

22. The lead of claim 21, wherein the heart/electrode interface contact impedance comprises approximately 1000 Ohm.

23. The lead of claim 19, wherein the active element comprises a microporous vitreous carbon material.

24. The lead of claim 19, wherein the body further comprises an axis and the plurality of protuberances are respectively positioned in said body at a distance from the axis and regularly distributed around said axis.

25. The lead of claim 24, wherein the plurality of protuberances further comprise three protuberances regularly distributed at 120° intervals around the axis.

26. The lead of claim 19, wherein the body contact surface has a diameter and each active element protuberance further comprises a cylindrical stem having a diameter between 15% and 30% of the diameter of the contact surface.

27. A lead for an active implantable medical device having an electrical conductor, comprising:

a cylindrical body having a distal end, an extremity, and a contact surface on said extremity, the body being made of an electrically insulated material, and a stimulation electrode, connected to said lead conductor, wherein the stimulation electrode comprises at least one active element having an exposed extremity tip, said exposed extremity tip protruding from said body contact surface, said active element presenting on at least a part of its exposed extremity tip a radius of curvature less than 0.5 mm;

wherein the lead contact surface has a meridian and the active element further comprises a flat form extending in a radial plane at the lead extremity, said flat form protruding from the contact surface along the meridian.

28. The lead of claim 27, wherein the contact surface comprises a hemispherical surface and the active element further comprises a flat disc shape.

29. The lead of claim 28 wherein the flat disc protrudes from said hemispherical contact surface by approximately 0.1 mm.

30. The lead of claim 27, wherein the active element further comprises two active elements each having a flat form, said two flat forms extending in two orthogonal radial planes to form the lead extremity.

31. The lead of claim 27 wherein, wherein the active element radius of curvature is not greater than 0.3 mm.

32. The lead of claim 27, wherein the lead further comprises a heart/electrode interface contact impedance of at least 800 Ohm.

33. The lead of claim 32, wherein the heart/electrode interface contact impedance comprises approximately 1000 Ohm.

34. The lead of claim 27, wherein the active element comprises a microporous vitreous carbon material.

* * * * *

UNITED STATES PATENT AND TRADEMARK OFFICE
CERTIFICATE OF CORRECTION

PATENT NO.    : 6,181,972 B1
DATED         : January 30, 2001
INVENTOR(S)   : Dominique Guedeney and Alain Bailly It is certified that error appears in the above-identified patent and that said Letters Patent is hereby corrected as shown below:

Column 1,
Line 40, delete "surface a" and insert -- surface and a -- therefor;

Column 2,
Line 62, delete "lead extremity lead" and insert -- lead extremity -- therefor;

Column 3,
Line 49, delete "with the lead a screw" and insert -- the lead with a screw -- therefor;
Line 55, delete "is proximal" and insert -- its proximal -- therefor;

Column 4,
Line 33, delete "surface areas" and insert -- surface area -- therefor;

Column 5,
Line 20, delete "geometry of" and insert -- geometry of the -- therefor;

Column 6,
Line 6, delete "bode contact" and insert -- body contact -- therefor;
Line 9, delete "further comprises" and insert -- further comprise -- therefor;
Line 25, delete "further comprises" and insert -- further comprise -- therefor;
Line 51, delete "surface" and insert -- surface; and -- therefor;

Column 7,
Line 6, delete "further comprises" and insert -- further comprise -- therefor;
Line 21, delete "0.5 mm:" and insert -- 0.5 mm; -- therefor;

UNITED STATES PATENT AND TRADEMARK OFFICE
CERTIFICATE OF CORRECTION

PATENT NO. : 6,181,972 B1
DATED : January 30, 2001
INVENTOR(S) : Dominique Guedeney and Alain Bailly It is certified that error appears in the above-identified patent and that said Letters Patent is hereby corrected as shown below:

<u>Column 8,</u>
Line 2, delete "further comprises" and insert -- further comprise -- therefor; and
Line 35, delete "wherein, wherein" and insert -- wherein -- therefor;

Signed and Sealed this

Twenty-eighth Day of June, 2005

JON W. DUDAS
*Director of the United States Patent and Trademark Office*